(12) United States Patent
Kegreiss et al.

(10) Patent No.: US 8,998,896 B2
(45) Date of Patent: Apr. 7, 2015

(54) TUBE CONNECTOR FOR A RADIO-FREQUENCY SURGICAL DEVICE, HANDLE FOR AN RF SURGICAL DEVICE, AND METHOD FOR CONNECTING TUBES FOR AN RF SURGICAL DEVICE TO SUCH A TUBE CONNECTOR

(75) Inventors: Horst Kegreiss, Tuebingen-Hirschau (DE); Britta Schwahn, Tuebingen (DE); Hansjoerg Bjoern Besch, Gomaringen (DE); Achim Brodbeck, Metzingen-Neuhausen (DE)

(73) Assignee: Erbe Elektromedizin GmbH, Tuebingen (DE)

( * ) Notice: Subject to any disclaimer, the term of this patent is extended or adjusted under 35 U.S.C. 154(b) by 434 days.

(21) Appl. No.: 13/498,039

(22) PCT Filed: Sep. 22, 2010

(86) PCT No.: PCT/EP2010/005807
§ 371 (c)(1),
(2), (4) Date: Mar. 23, 2012

(87) PCT Pub. No.: WO2011/035902
PCT Pub. Date: Mar. 31, 2011

(65) Prior Publication Data
US 2012/0245584 A1 Sep. 27, 2012

(30) Foreign Application Priority Data

Sep. 24, 2009 (DE) .......... 10 2009 042 948
Nov. 6, 2009 (DE) .......... 10 2009 052 208

(51) Int. Cl.
*A61B 18/00* (2006.01)
*A61B 18/12* (2006.01)
*H01R 13/00* (2006.01)

(52) U.S. Cl.
CPC ....... *A61B 18/12* (2013.01); *A61B 2018/00916* (2013.01); *H01R 13/005* (2013.01)

(58) Field of Classification Search
None
See application file for complete search history.

(56) References Cited

U.S. PATENT DOCUMENTS 3,234,317 A 2/1966 Henderson
3,909,506 A 9/1975 Campari et al.
(Continued)

FOREIGN PATENT DOCUMENTS

DE 202006015697 U1 3/2007
EP 0164993 A2 12/1985
(Continued)

OTHER PUBLICATIONS

Russian Office Action for RU 2012114919/14 (022555), English translation attached to original, Dated Oct. 10, 2013, All together 10 Pages.
(Continued)

*Primary Examiner* — Brian T Gedeon
(74) *Attorney, Agent, or Firm* — Brooks Kushman P.C.

(57) ABSTRACT

A tube connector for a radio-frequency surgical device, having two end sleeves, which are each provided with an axial through channel and connected to each other by a web extending from a wall plane of the first end sleeve axially in the direction of the second end sleeve. The web being at least partially made of an electrically conductive material, and the respective end sleeves can be compressed or crimped in some regions for fixing a tube, which can be arranged in the respective through channel. Also disclosed is a handle for an RF surgical device, and to a method for connecting tubes for an RF surgical device to such a tube connector.

16 Claims, 2 Drawing Sheets

(56) References Cited

U.S. PATENT DOCUMENTS

Figure 1:
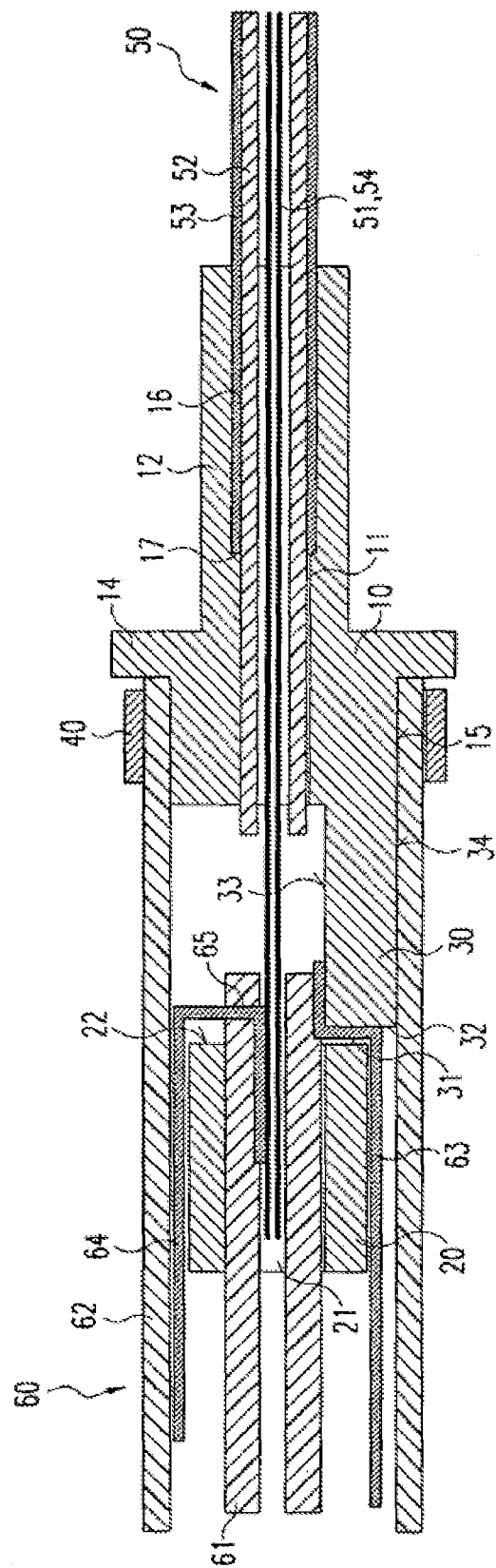

| | | |
|---|---|---|
| 4,466,690 A | 8/1984 | Osypka |
| 2008/0122222 A1 | 5/2008 | Sheppard |

FOREIGN PATENT DOCUMENTS

| | | |
|---|---|---|
| EP | 0164993 A3 | 12/1985 |
| JP | 0663994 | 9/1994 |
| JP | 08185909 | 7/1996 |
| JP | 2002113539 | 4/2002 |
| RU | 2354327 | 5/2009 |
| RU | 2357077 | 5/2009 |
| WO | 9512225 | 5/1995 |
| WO | 2007002179 A2 | 1/2007 |
| WO | 2007002179 A3 | 1/2007 |

OTHER PUBLICATIONS

Japanese Office Action for JP2012-530165, English Translation attached to original, Dated Dec. 17, 2013, All together 12 Pages.
International Search Report for PCT/EP2010/005807, English translation attached to original, Both completed by the European Patent Office on Dec. 14, 2010, All together 7 Pages.
International Preliminary Report on Patentability and Written Opinion for PCT/EP2010/005807, Date of issuance of this report Apr. 3, 2012, Issued by the International Bureau of WIPO, All together 8 Pages.
Russian Notification of the results of examination of patentability for Russian Application No. 2012114919/14, English Translation attached to original, Completed by the Russian Patent Office, Dated Jun. 19, 2014, All together 12 Pages.

TUBE CONNECTOR FOR A RADIO-FREQUENCY SURGICAL DEVICE, HANDLE FOR AN RF SURGICAL DEVICE, AND METHOD FOR CONNECTING TUBES FOR AN RF SURGICAL DEVICE TO SUCH A TUBE CONNECTOR

CROSS-REFERENCE TO RELATED APPLICATION

This application is the U.S. national phase of PCT Appln. No. PCT/EP2010/005807 filed Sep. 22, 2010, which claims priority to German application 10 2009 042 948.4 filed on Sep. 24, 2009 and German application 10 2009 052 208.5 filed on Nov. 6, 2009 the disclosures of which are incorporated in their entirety by reference herein.

The invention relates to a tube connector for an electrosurgical device, a handle for an electrosurgical device, and to a method for connecting tubes for an electrosurgical device using such a tube connector.

Electrosurgical devices, as are produced and distributed by the applicant for example, are well known. Such devices usually comprise an RF generator, which generates a radiofrequency, therapeutically effective electric current. By way of example, in the known devices, the RF current is applied by means of a probe, which can be inserted into the body of a patient. The probe comprises a device-side tube section and a probe-side tube section. A handle comprising operating elements for the electrosurgical device is typically arranged between the device-side tube section and the probe-side tube section.

Known electrosurgical devices often make use of bipolar probes, which comprise an additional gas supply such that an RF current application can take place in a protective gas atmosphere. To this end, the probe-side tube section and the device-side tube section respectively have a tube line, which are pneumatically connected in the region of the handle. Furthermore, the electrical lines, which are required to transmit the RF current to the probe tip, are electrically coupled to one another in the region of the handle. In the case of bipolar probes, two separate electrical connections are required to this end in the region of the handle.

In practice, it was found to be difficult and complicated to connect the individual electrical conductors and the gas lines arranged coaxially within one another, particularly as a result of the small dimensions in the case of electrosurgical probe tubes. A further difficulty arises from the different dimensions of the probe-side tube section and the device-side tube section. Connecting the individual components of the device-side tube section and the probe-side tube section according to previous concepts furthermore entails a relatively complicated design with a relatively high number of individual components and an accordingly very complicated assembly. Moreover, such concepts were found to be susceptible to faults.

It is an object of the invention to specify a tube connector that has a simple design and by means of which the assembly complexity is reduced when establishing connections of electrosurgical tube systems. Furthermore, the invention is based on the object of specifying a handle for an electrosurgical device and a method for connecting tubes for an electrosurgical device using such a tube connector.

According to the invention, this object is achieved by the subject matter of patent claim 1 in respect of the tube connector, by the subject matter of patent claim 9 in respect of the handle and by the subject matter of patent claim 10 in respect of the method.

The invention is based on the idea of specifying a tube connector for an electrosurgical device with two end sleeves which each have an axial through-channel and are interconnected by a web. From a wall plane of the first end sleeve, the web extends axially in the direction of the second end sleeve. At least the web at least in sections comprises an electrically conductive material. The end sleeves can each be compressed or crimped in sections in order to affix a tube which can be arranged in the respective through-channel.

The tube connector according to the invention allows a simple and safe electrical, and at the same time pneumatic, connection of tube lines of an electrosurgical device. In doing so, the tube connector has a relatively simple design, and so it is easier to assemble the electrosurgical device. In particular, gastight pneumatic contacting is achieved in each case by compressing or crimping the end sleeves. The electrical contacts can likewise be established by the crimping, with the invention not being restricted to this. The electrical and pneumatic connection can thus be established simultaneously by means of few assembly steps, namely crimping or clamping, and the time expenditure for assembling the electrosurgical device can be reduced. In particular, the simple contacting of the electrical conductors using the tube connector makes a tube connection possible in relatively little space. Hence, the spatial requirement for the tube connection, for example in a handle, is reduced. Moreover, these advantages can be achieved using only a single component, namely the tube connector according to the invention, whereas previous connection concepts have resorted to a plurality of different connection elements in order to connect the electrical and pneumatic tube components.

The electrically conductive material of the tube connector ensures a safe and stable electrical connection between the device tube and the probe tube. In addition, the electrically conductive material enables a reduction in the assembly complexity because the electrical connection between the device tube and the probe tube is not established directly, as was conventional until know, but rather indirectly using the tube connector.

In a preferred embodiment of the tube connector according to the invention, the first end sleeve comprises a probe-side section and a device-side section, with the probe-side section having a smaller cross-sectional diameter than the device-side section. This embodiment particularly advantageously allows the transfer from a device tube with a relatively larger cross-sectional diameter to a probe tube with a relatively smaller diameter. In other words, the tube connector according to the invention can be used to connect a probe tube to a device tube of the electrosurgical device, even if the probe tube has a significantly smaller cross-sectional diameter than the device tube. In doing so, the tube connector simultaneously ensures a pressure-resistant, i.e. low leakage or no leakage, pneumatic connection and a safe and stable electrical connection between the probe tube and the device tube.

Furthermore, the first end sleeve can have a larger cross-sectional diameter than the second end sleeve. The device-side section of the first end sleeve in particular has a larger cross-sectional diameter than the second end sleeve. What this makes possible is that the tube connector achieves a simple connection between a probe-side tube and a device-side tube, which is embodied as a coaxial line. In this context, a coaxial line is understood to mean an arrangement of two tube-like lines, with an inner, tube-like line being routed coaxially within an outer, tube-like line. Here, free space is formed between the inner line and the outer line. In this constellation, the different cross-sectional diameter of the second end sleeve and the first end sleeve, in particular in conjunction with the web connecting the end sleeves, enables separate coupling of both the lumen of the outer line of the device tube to the probe tube and the lumen of the inner line of the device tube to the probe tube.

The second end sleeve and/or the web preferably comprise a bore, which extends at least in part in the radial direction. The bore enables the contacting of an electrical conductor with the electrically conductive tube connector in a particularly simple manner. By way of example, the bore can be aligned such that an electrical conductor, when inserted through the bore from the outside, projects into the second through-channel. By inserting an inner coaxial tube into the second through-channel, the electrical conductor is then bent and clamped between the inner coaxial tube and the tube connector. Alternative connection options, for example soldering or adhesive bonding, are possible.

A further advantageous embodiment of the invention provides for the bore in the web extending between the first and second end sleeves to be flush with an axial boundary face, facing the first end sleeve, of the second end sleeve. Such an arrangement of the bore is advantageous both from a manufacturing-technical point of view when producing the tube connector and from an assembly-technical point of view when connecting the tubes of the electrosurgical device. In particular, this special arrangement of the bore enables a simple electrical connection between a first electrical conductor of the device tube and the tube connector and, thereafter, the probe tube.

The first end sleeve preferably comprises a shoulder, which is arranged between the probe-side section and the device-side section and has a larger cross-sectional diameter than the device-side section. As a result of the larger cross-sectional diameter compared to the device-side section of the first end sleeve, the shoulder can form a connection element for connecting the tube connector with surrounding parts, e.g. a handle for an electrosurgical device. The special arrangement of the shoulder between the device-side section and the probe-side section is advantageous from a manufacturing-technical point of view, particularly if the probe-side section has a smaller cross-sectional diameter than the device-side section.

According to a further preferred embodiment of the tube connector according to the invention, provision can be made for an outer crimping sleeve, which engages around the device-side section of the first end sleeve in an annular manner and can, at least in regions, be compressed radially in order to affix a device-side tube. The outer crimping sleeve enables a simple fixation of the device tube on the tube connector, more particularly the device-side section of the first end sleeve, by a radial deformation. This deformation, which is referred to as crimping or clamping, thus forms a force-fit and interlocking connection between the outer crimping sleeve, the device tube and the device-side section of the first end sleeve.

According to a coordinate aspect, the invention is based on the idea of specifying a tube system for an electrosurgical device with a tube connector as per claim 1.

A further coordinate aspect of the invention relates to a method for connecting tubes for an electrosurgical device using a tube connector as claimed in claim 1, comprising the following steps:
A probe tube is arranged in a first through-channel of the first end sleeve and an inner device tube is arranged in a second through-channel of the second end sleeve;
a first electrical conductor is arranged between the web and the inner device tube; and at least one, more particularly two, first gastight connections are introduced into the first end sleeve and at least one second gastight connection is introduced into the second end sleeve.

In respect of the effects and advantages of the method according to the invention, reference is made to the explanations in respect of the tube connector described at the outset.

In a preferred embodiment, the first gastight connection comprises a first crimping and/or the second gastight connection comprises a second crimping. Utilizing a crimping process for establishing the gastight connections is advantageous, particularly when establishing the tube connection under cleanroom conditions. Moreover, the crimping at the same time enables clamping of the electrical connections, and so an additional work step is saved.

The first electrical conductor can be inserted into the second through-channel via an axial boundary face, facing the first end sleeve, of the second end sleeve or a bore, which extends at least in part in the radial direction through the second end sleeve or the web. In any case, it is expedient for the second electrical conductor to be arranged within the second end sleeve, preferably in the second through-channel, and the first electrical conductor to be affixed within the second end sleeve, for example between the second end sleeve and an inner device tube. By way of example, the fixation can be brought about by clamping. However, it is not precluded that the first electrical conductor is also affixed by crimping the second end sleeve or by a bonded connection, for example a soldered or adhesive connection.

In the case of a further preferred embodiment of the method according to the invention, an outer device tube is routed via a device-side section of the first end sleeve and enclosed by a crimping sleeve, into which a third crimping is introduced in order to affix the outer device tube.

In a further preferred embodiment of the method, provision is made for a second electrical conductor to be routed through an opening of the inner device tube and electrically connected to a nozzle pipe, which extends coaxially from a probe tube into the inner device tube.

The electrical connections between the device tube and the probe tube are preferably fixed by clamping. Thus, the electrical conductors are clamped between the tube connector and the device tube, more particularly between the inner device tube and the second end sleeve. The clamping connection is fixed by the crimping of the second end sleeve.

Figure 2:
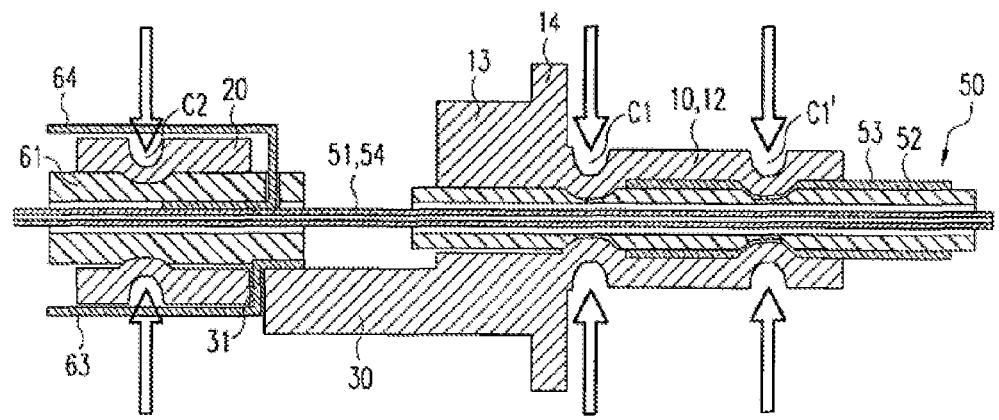
Figure 3:
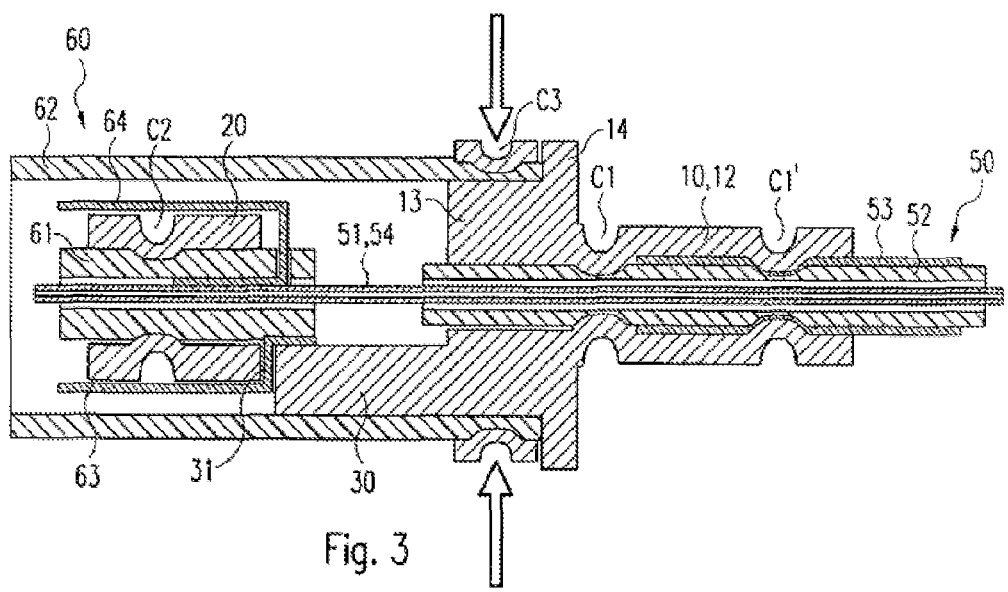

In the following text, the invention will be explained in more detail with reference to the attached, schematic drawings, in which:

FIG. 1 shows a longitudinal section through a tube connector according to the invention as per a preferred exemplary embodiment; and FIGS. 2 and 3 show different method steps for connecting tubes from an electrosurgical device using the tube connector as per FIG. 1.

The tube connector as per the exemplary embodiment according to FIG. 1 comprises a first end sleeve 10 and a second end sleeve 20, with the end sleeves 10, 20 being interconnected by a web 30. The tube connector, more particularly the end sleeves 10, 20 and the web 30, has an integral design. The end sleeves 10, 20 respectively have a rotationally symmetric shape and are aligned coaxially with respect to one another. In particular, the end sleeves 10, 20 respectively comprise one through-channel 11, 21, with the through-channels 11, 21 being arranged flush with one another or coaxially. The end sleeves 10, 20 are arranged at a distance from one another in the longitudinal direction of the tube connector, with the distance between the end sleeves 10, being determined by the length of the web 30.

The first end sleeve 10 comprises a first through-channel 11, in which a probe tube 50 is or can be arranged during use. Here, the cross-sectional diameter of the first through-channel 11 substantially corresponds to the cross-sectional diameter of the probe tube 50. In the region of an axial outer end of the tube connector, the first end sleeve 10 has an axial bore 16, which extends over part of the length of the first through-channel 11. The axial bore 16 has a larger cross-sectional diameter than the first through-channel 11 and substantially forms a widened section of the first through-channel 11. The axial border of the axial bore 16 forms a stop 17, which forms the transition between the relatively smaller cross-sectional diameter of the first through-channel 11 and the relatively larger cross-sectional diameter of the axial bore 16. During use, i.e. when the tube connector is coupled to a probe tube 50, the axial bore 16 accommodates a first probe conductor 53 of the probe tube 50.

The first probe conductor 53 forms the radial circumferential border of the probe tube 50. An outer probe tube 52, which serves as gas return, is arranged within the first probe conductor 53. Furthermore, the probe tube 50 comprises a nozzle pipe 51, arranged coaxially within the probe tube 50 and having a substantially smaller cross-sectional diameter than the outer probe tube 52, for supplying gas to the probe. The nozzle pipe 51 essentially forms an inner probe tube. This is how two gas lines arranged coaxially within one another are provided by the probe tube 50. In this case, the nozzle pipe 51 furthermore serves as second probe conductor 54. The probe conductors 53, 54 form the electrical connection to bipolar electrodes at the probe tip. Thus, the probe conductors 53, 54 have an electrically conductive material. In the process, the nozzle pipe 51 makes it possible to supply a coolant into the region of the probe tip or into the treatment region. The coolant can be returned to the electrosurgical device via the gas line formed by the outer probe tube 52.

In this context, reference is made to the fact that if a protective gas is used instead of a coolant, a gas return is not mandatory. Hence, it is possible that merely a gas supply, for example via the nozzle pipe 51, is provided if a protective gas is used. The protective gas escapes at the probe tip and is released at the treatment site. By contrast, it is expedient to provide the gas return if a coolant, more particularly a coolant gas, is used in order to let the coolant flow through the probe tip in a cooling circuit.

In addition to the probe-side section 12, which comprises the axial bore 16, the first end sleeve 10 has a device-side section 13, which is separated from the probe-side section 12 by a shoulder 14. The device-side section 13 has a larger cross-sectional diameter than the probe-side section 12. The shoulder 14, which is arranged between the device-side section 13 and the probe-side section 12, in turn has a larger cross-sectional diameter than the device-side section 13. Thus, the shoulder 14 forms a rib encircling the circumference of the tube connector, which makes it possible to connect the tube connector to further external components, for example a handle of an electrosurgical device.

From the device-side section 13, the web 30 extends in the direction of the second end sleeve 20. Here, the web has an outer face 34, which is flush with an outer circumferential face 15 of the device-side section 13. In the circumferential direction, the web 30 extends in part over the circumference of the device-side section 13. Thus, the web 30 is substantially formed from a circle segment of the device-side section 13, which is extended in the direction of the second end sleeve 20. Furthermore, the web 30 has an inner face 33, which is flush with a second through-channel 21 of the second end sleeve 20. Here, the inner face 33 can correspondingly reproduce the curvature of the second through-channel 21, formed in the circumferential direction. Alternatively, it is also possible for the inner face 33 to be embodied in a flat or areal manner and to be aligned substantially tangentially with respect to the curvature of the second through-channel 21.

A step 32 resulting from the different cross-sectional diameters of the end sleeves 10, 20 is formed at a longitudinal end of the web 30 facing the second end sleeve 20. In particular, the second end sleeve 20 has a smaller cross-sectional diameter than the first end sleeve 10. The radial bore 31, which is flush first with the step 32 and secondly with an axial boundary face 22 of the second end sleeve 20, is associated with the web 30. Here, the flush arrangement of the bore 31 relates to the inner face of the bore, which defines the bore diameter, and to the axial boundary face 22, arranged in a corresponding tangential manner thereto, or to the step 32, aligned tangential with respect thereto.

As an alternative thereto, the bore 31 can have an oblique angle of incidence, and so the bore axis of the bore 31 forms an angle with respect to the longitudinal axis of the through-channels 11, 21 that is not equal to 90°. In this case, the bore 31 is preferably aligned such that the bore axis substantially extends in the direction of the first end sleeve 10. What this achieves is that an electrical conductor that, through the bore 31, extends into the region of the second through-channel or into the region between the first through-channel 11 and the second through-channel 21 can simply be bent and clamped by the inner device tube 61.

Thus, the bore 31 serves for the simple electrical connection between a first electrical conductor 63 and the tube connector. A bore 31 is not provided in alternative embodiments. By way of example, the first electrical conductor 63 can instead be inserted into the second through-channel 21 of the second end sleeve 20 via the axial boundary face 22. In the process, the first electrical conductor 63 can, in the second through-channel, be clamped, soldered, adhesively bonded or electrically connected in another manner to the tube connector.

Reference is made to the fact that the transition between the individual sections of the tube connector, in particular the transition from the web 30 to the second end sleeve 20, can generally be embodied in different manners. By way of example, the web 30 can taper off toward the end sleeve 20 such that the step 32 runs substantially obliquely or forms a curve or a bevel. The step 32 can have the shape of a cone segment. It is furthermore possible that the web 30, particularly if it is formed as a continuation of a circle segment of the device-side section 13, forms a transition to the respective end sleeve 10, 20, in which transition the circle segment imaged in the cross section of the web 30 becomes enlarged. In other words, the web 30 can also have a shape like a canoe.

The second end sleeve 20 has a substantially cylindrical or tube-like design. Thus, the second end sleeve 20 forms a substantially pipe-shaped component, which encloses the second through-channel 21. During use, the device tube 60, more particularly an inner device tube 61, is or can be arranged in the second through-bore 21, i.e. in the second end sleeve 20. Furthermore, during use, the second end sleeve 20 is or can be arranged within an outer device tube 62 of the device tube 60.

A device tube 60 and a probe tube 50 are connected to the tube connector as follows:

The device tube 60 comprises an inner device tube 61 and an outer device tube 62, with the inner device tube 61 being arranged coaxially within the outer device tube 62. The free space formed between the inner device tube 61 and the outer device tube 62 serves as gas return in this case, whereas the lumen of the inner device tube 61 forms a gas supply. Furthermore, two electrical conductors 63, 64 are arranged in the interspace between the inner and outer device tubes 61, 62. The electrical conductors 63, 64 are electrically coupled to the electrosurgical device for transmitting electrical energy into the RF probe. The further connection of the electrical conductors 63, 64 with the corresponding probe conductors 53, 54 is brought about using the tube connector, which comprises an electrically conductive material. Here, the first electrical conductor 63 is routed through the bore 31 from the outside such that an end section of the first electrical conductor 63 comes to rest in front of the second through-channel 21 of the second end sleeve 20. Alternatively, the first electrical conductor 63 is directly introduced or inserted into the second through-channel 21, with the access to the second through-channel 21 being possible both over the boundary face 22 facing the first end sleeve 10 and over an axial end face 23 of the second end sleeve 20. The inner device tube 61 is thereupon routed through the second through-channel 21, with the inner device tube 61 bending the end section of the first electrical conductor 63 after passing through the second end sleeve 20 such that said conductor is clamped between the inner device tube 61 and the inner face 33 of the web 30. The second electrical conductor 64 is subsequently routed through a radial opening 65, which is arranged in an end section of the inner device tube 61. Here, the second electrical conductor 64 is routed through the radial opening 65 from the outside until an end section of the second electrical conductor 64 comes to rest within the lumen of the inner device tube 61. Analogously to the alternative connection of the first electrical conductor 63, the second electrical conductor 64 can also be inserted into the lumen of the inner device tube 61 via an end face of the inner device tube 61.

In a further, subsequent step the outer device tube 62 is then routed via the second end sleeve 20, the web 30 and, finally, the device-side section 13 of the first end sleeve 10. Here, the shoulder 14 of the first end sleeve forms a stop for the outer device tube 62. As additionally illustrated in FIG. 1, provision is furthermore made for a crimping sleeve 40 for connecting or affixing the device tube 60 to the tube connector, which crimping sleeve has an annular shape and is arranged in the region of the device-side section 13. In this case, the crimping sleeve 40 encloses the outer device tube 62. What this means is that the crimping sleeve 40 has a larger cross-sectional diameter than the device-side section 13 of the first end sleeve 10. Furthermore, the crimping sleeve 40 has a smaller cross-sectional diameter than the shoulder 14, and so the shoulder 14 also forms a stop for the crimping sleeve 40. According to the exemplary embodiment illustrated in the figures, there is no connection between the crimping sleeve 40 and the first end sleeve 10. However, it is also possible for the crimping sleeve 40 to be fixedly or detachably coupled to the shoulder 14 of the first end sleeve 10. By way of example, the crimping sleeve 40 and the shoulder 14 may have an integral design such that the crimping sleeve 40 substantially forms an annular rib extending from the shoulder 14 in the axial direction. In this case, the crimping sleeve 14 delimits an annular groove, into which the outer device tube 62 can be inserted.

The probe tube 50 is coupled to the tube connector before or after the outer device tube 62 is connected to the first end sleeve 10. The probe tube 50 comprises the outer probe tube 52, which has a first probe conductor 53, arranged on the external circumference, and the nozzle pipe 51, which simultaneously serves as second probe conductor 54. As described above, the outer probe tube 52 is inserted into the first through-channel 11 of the first end sleeve 10, with the first probe conductor 53 being arranged in the axial bore 16. The outer probe tube 52, or the probe tube 50 in general, is preferably arranged in the first through-channel 11 such that an end section of the outer probe tube 52 projects beyond the device-side section 13 of the first end sleeve 10. The nozzle pipe 51, which extends beyond the outer probe tube 52, is arranged within the outer probe tube 52. Thus, the nozzle pipe 51 projects beyond the outer probe tube 52 in the direction of the device tube 60. This allows the nozzle pipe 51 to extend into the inner device tube 61 over the distance between the end sleeves 10, 20 of the tube connector. When the nozzle pipe 51 is inserted into the inner device tube 61, the end section of the second electrical conductor 64 of the device tube 60 is bent in the process and clamped between the nozzle pipe 51 and the inner device tube 61. The nozzle pipe 51 comprises an electrically conductive material and, in the arrangement illustrated in FIG. 1, constitutes an electrical connection between the probe tip and the second electrical conductor 64.

In this context, reference is made to the fact that the spacing in the radial direction between the nozzle pipe and the inner device tube 61 has been displayed for illustrative purposes. In actual fact, provision is made for the nozzle pipe 51 to be connected to the inner device tube 61 in a substantially fluid-tight or pressure-tight manner.

In order to fix the connection between the device tube 60 and the probe tube 50 by means of the tube connector, crimpings, i.e. force-fit and interlocking connections, are placed at selected points on the tube connector. Preferred connections are illustrated in FIGS. 2 and 3. In particular, FIG. 2 shows two first crimpings C1, C1', which are introduced in the region of the probe-side section 12 of the first end sleeve 10. A different number of crimpings, more particularly a single crimping or more than two crimpings, are possible. In the exemplary embodiment as per FIG. 2, provision is made for one of the first crimpings C1 to be introduced in a region of the probe-side section 12 that adjoins the shoulder 14. A further first crimping C1 is introduced in the region of the axial bore 16 of the probe-side section 12. A fixed connection between the first probe conductor 53 and the tube connector is established by the further first crimping C1' in particular. A second crimping C2 is subsequently introduced into the second end sleeve 20 in order to affix the inner device tube 61 in the second end sleeve 20. The outer device tube 62 is fixedly connected to the first end sleeve 10 by a third crimping C3. Here, the third crimping C3 is introduced into the crimping sleeve 40, which thus clamps the outer device tube 62 against the device-side section 13 of the first end sleeve 10.

In general, the crimping connections enable a gastight connection of the tubes to the tube connector. This particularly applies to the first crimping C1 and the second crimping C2, with the first crimping C1 coupling the outer probe tube 52 to the tube connector, more particularly the first end sleeve 10, in a gastight manner. The second crimping C2 brings about gastight coupling between the second end sleeve 20, the inner device tube 61 and (not displayed in the figures for illustrative purposes) the nozzle pipe 51 of the probe tube 50. Thus, the nozzle pipe 51 forms a support for the second crimping C2 such that the inner device tube 61 is not pinched off. Rather, the inner device tube 61 is sealed with respect to the nozzle pipe 51 in a gastight manner. This is how a gastight gas supply is provided via the inner device tube 61 and the nozzle pipe 51.

After gastight contacting, the gas return is brought about using the tube connector, more particularly the first crimping C1 and the third crimping C3 (FIG. 3), via the outer probe tube 52 and the outer device tube 62. The gas connection between the outer device tube 62 and the outer probe tube 52 is enabled by the web 30 between the end sleeves 10, 20 since the web 30 serves as a spacer between the first end sleeve 10 and the second end sleeve 20. The first further crimping C1' primarily enables the electrical contacting between the first probe conductor 53 and the electrically conductive tube connector. In order to ensure a gastight connection, provision is made for the first crimping C1, which is introduced in a region of the first end sleeve 10 that is free from additional components, more particularly the first probe conductor 52. Analogously to the crimping connections in the first end sleeve 10, a double crimping can also be provided in the second end sleeve 20, with the second crimping C2 ensuring the gastight connection between the inner device tube 61 and the nozzle pipe 51, and a further second crimping ensuring the fixation of the electrical contacts, more particularly the first and second electrical conductor 63, 64.

Electrical contacting is preferably brought about by clamping the two parallel electrical conductors 63, 64 between the inner device tube 61 of the device tube 60 and the electrically conductive tube connector, or on the electrically conductive nozzle pipe 51. Other electrical contact connections, e.g. soldered connections or windings, are possible. The second electrical conductor 64 in particular can be wound around the nozzle pipe 51 for the purposes of establishing electrical contact.

In the exemplary embodiment illustrated in the figures, the first electrical conductor 63 is routed through the bore 31 of the tube connector and clamped with the second end sleeve 20 when the inner device tube 61 is inserted into the second end sleeve 20, and electrically contacted as a result of that. The aforementioned clamping between the first electrical conductor 63 and the inner device tube 61 is fixed and secured by crimping the inner device tube 61 onto the nozzle pipe 51 (crimping C2) in the region of the second end sleeve 20. At the same time, the crimping C2 realizes a connection between the coaxial gas lines, namely the inner device tube 61 and the nozzle pipe 51.

In order to establish the electrical contact of the gas system to the outside, the current is transmitted by crimping (further first crimping C1') to the first probe conductor 53, which is arranged on the outer circumference of the outer probe tube 52, via the tube connector or the multiple-crimping sleeve. This is how the electrical contact is established between the first electrical conductor 63 and the first probe conductor 53.

The second electrical conductor 64 is likewise fixed by clamping and, as a result thereof, is electrically contacted by the tube connector or the multiple-crimping sleeve. The second electrical conductor 64 is routed into the lumen of the inner device tube 61 through the radial opening 65 in the inner device tube 61 of the device tube 60. During the subsequent insertion of the nozzle pipe 51 into the inner device tube 61, the second electrical conductor 64 is clamped by the nozzle pipe 51 or the inner device tube 61 and, as a result, establishes electrical contact to the nozzle pipe 51, which forms the second probe conductor 54. The electrical contact between the second electrical conductor 64 and the nozzle pipe 51 or second probe conductor 54 is fixed by the crimping C2, which is introduced into the second end sleeve 20. Thus, the nozzle pipe 51 simultaneously forms the electrically conductive second probe conductor 54 and the inner gas line, more particularly the gas supply, of the probe tube 50.

The described tube connector or the multiple-crimping sleeve furthermore enables the coaxial gas line of the device tube 60 to be converted into a coaxial gas line of the probe tube 50, with the probe tube 50 having a smaller cross-sectional diameter than the device tube 60. This change in diameter allows the endoscopic use of the electrosurgical device. In the process, it is expedient if the connections between the device tube 60 and the probe tube 50 are gastight and pressure resistant.

To this end, the inner device tube 61 is crimped to the nozzle pipe 51 in the second end sleeve 20 of the tube connector, with two electrical contacts being established here at the same time (crimping C2). The outer device tube 62 of the device tube 60 is crimped onto the tube connector or the multiple-crimping sleeve in a gastight manner via the crimping sleeve 40 (crimping C3). The gas line from the outer device tube 60 to the outer probe tube 52 is brought about via an opening in the multiple-crimping sleeve or in the tube connector, with the nozzle pipe 51 also running through said opening. Hence, the opening corresponds to the distance between the end sleeves 10, 20, which is spanned by the web 30. Hence, the opening forms a fluid connection between the lumen of the outer device tube 62 and the first end sleeve 10. The first end sleeve 10 brings about both electrical contacting to the first probe conductor 53 using the further first crimping C1' and, offset thereto, the gastight crimping of the multiple-crimping sleeve or tube connector onto the outer probe tube 52 (first crimping C1).

The invention is particularly suitable for connecting tubes for electrosurgical devices, more particularly electrosurgical devices that can be used for endoscopy. Embodiments of the invention that dispense with special connection techniques, for example adhesive bonding or soldering, are particularly suitable for connecting tubes for electrosurgical devices under cleanroom conditions. Thus, the invention provides a tube connection that is suitable for cleanrooms. Since the tube connector advantageously forms a single component, the suitability as disposable product is ensured. The tube connector or the multiple-crimping sleeve preferably comprises an electrically conductive metal such that it is furthermore ensured that the tube connector can withstand increased gas pressure. Thus, the tube connector forms a safe, more particularly gastight, connection between the tubes of an electrosurgical device.

LIST OF REFERENCE SIGNS

10 First end sleeve
11 First through-channel
12 Probe-side section
13 Device-side section
14 Shoulder
15 Outer circumferential face
16 Axial bore
17 Stop
20 Second end sleeve
21 Second through-channel
22 Axial boundary face
23 End face
30 Web
31 Bore
32 Step
33 Inner face
34 Outer face
40 Crimping sleeve
50 Probe tube
51 Nozzle pipe
52 Outer probe tube
53 First probe conductor
54 Second probe conductor
60 Device tube 61 Inner device tube
62 Outer device tube
63 First electrical conductor
64 Second electrical conductor
65 Radial opening
C1 First crimping
C1' Further first crimping
C2 Second crimping
C3 Third crimping

The invention claimed is:

1. A tube connector for an electrosurgical device comprising:
    two end sleeves which each have an axial through-channel and are interconnected by a web extending axially from a first end sleeve in a direction of a second end sleeve, wherein at least the web at least in sections has an electrically conductive material and the first and second end sleeves can each be compressed or crimped in sections to affix a tube which can be arranged in the through-channel.

2. The tube connector of claim 1, wherein the first end sleeve comprises a probe-side section and a device-side section, the probe-side section having a smaller cross-sectional diameter than the device-side section.

3. The tube connector of claim 1, wherein the device-side section of the first end sleeve has a larger cross-sectional diameter than the second end sleeve.

4. The tube connector of claim 1, wherein the second end sleeve and/or the web comprise a bore, wherein the bore extends at least in part in a radial direction.

5. The tube connector of claim 4, wherein the bore is flush with an axial boundary face, facing the first end sleeve, of the second end sleeve.

6. The tube connector of claim 2, wherein the first end sleeve comprises a shoulder arranged between the probe-side section and the device-side section, and wherein the shoulder has a larger cross-sectional diameter than the device-side section.

7. The tube connector of claim 1, wherein an outer crimping sleeve engages around the device-side section of the first end sleeve in an annular manner and is optionally radially compressible, at least in regions, to affix a device-side tube.

8. The tube connector of claim 1, wherein the second end sleeve and/or the web comprise at least one soldering region and/or a clamping region.

9. A tube system for an electrosurgical device comprising the tube connector of claim 1.

10. A method for connecting tubes for an electrosurgical device comprising connecting the tubes with a tube connector of claim 1.

11. The method of claim 10, comprising the following steps:
    arranging a probe tube in a first through-channel of the first end sleeve and arranging an inner device tube in a second through-channel of the second end sleeve;
    arranging a first electrical conductor between the first end sleeve and the inner device tube, and
    introducing at least one first gastight connection into the first end sleeve and introducing at least one second gastight connection into the second end sleeve.

12. The method of claim 11, wherein the first gastight connection comprises a first crimping and/or the second gastight connection comprises a second crimping.

13. The method of claim 10 further comprising the step of inserting the first electrical conductor into the second through-channel via an axial boundary face, facing the first end sleeve, of the second end sleeve or a bore, which extends at least in part in a radial direction through the second end sleeve or the web.

14. The method of claim 11 further comprising the step of routing an outer device tube via a device-side section of the first end sleeve enclosing the outer device tube by a crimping sleeve, and introducing a third crimping into the crimping sleeve to affix the outer device tube.

15. The device of claim 11, wherein a second electrical conductor is routed through an opening of the inner device tube and electrically connected to a nozzle pipe, which extends coaxially from a probe tube into the inner device tube.

16. The method of claim 11 further comprising the step of introducing two first gastight connections into the first end sleeve.

* * * * *